US006645905B2

(12) United States Patent
Gaffney et al.

(10) Patent No.: US 6,645,905 B2
(45) Date of Patent: Nov. 11, 2003

(54) ANNEALED AND PROMOTED CATALYST

(75) Inventors: Anne Mae Gaffney, West Chester, PA (US); Michele Doreen Heffner, Chalfont, PA (US); Ruozhi Song, Wilmington, DE (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 10/117,904

(22) Filed: Apr. 8, 2002

(65) Prior Publication Data
US 2002/0183198 A1 Dec. 5, 2002

Related U.S. Application Data
(60) Provisional application No. 60/286,278, filed on Apr. 25, 2001.

(51) Int. Cl.$^7$ ................................. B01J 23/00
(52) U.S. Cl. ........................ 502/311; 502/312; 558/323
(58) Field of Search ................................. 502/311, 312; 558/323

(56) References Cited

U.S. PATENT DOCUMENTS

| 5,281,745 A | * | 1/1994 | Ushikubo et al. | ........... 558/319 |
| 5,380,933 A | | 1/1995 | Ushikubo et al. | |
| 6,043,186 A | | 3/2000 | Komada et al. | |

FOREIGN PATENT DOCUMENTS

| EP | 1192986 A | 4/2002 |
| JP | 7-53448 | 2/1995 |

OTHER PUBLICATIONS

Translation of Japanese Laid–Open Patent Application Publication No. 6–228073 (Aug. 16, 1994).
Translation of Japanese Laid–Open Patent Application Publication No. 10–330343 (Dec. 15, 1998).
Translation of Japanese Laid–Open Patent Application Publication No. 11–43314 (Feb. 16, 1999).

* cited by examiner

Primary Examiner—Joseph K. McKane
Assistant Examiner—Kamal Saeed

(57) ABSTRACT

A mixed metal oxide, which may be an orthorhombic phase material, is improved as a catalyst for the production of unsaturated carboxylic acids, or unsaturated nitriles, from alkanes, or mixtures of alkanes and alkenes, by: contacting with a liquid contact member selected from the group consisting of organic acids, alcohols, inorganic acids and hydrogen peroxide to form a contact mixture; recovering insoluble material from the contact mixture; calcining the recovered insoluble material in a non-oxidizing atmosphere; admixing the calcined recovered insoluble material with (i) at least one promoter element or compound thereof and (ii) at least one solvent for the at least one promoter element or compound thereof; removing the at least one solvent to form a catalyst precursor; and calcining the catalyst precursor.

2 Claims, No Drawings

ANNEALED AND PROMOTED CATALYST

CROSS REFERENCE TO RELATED PATENT APPLICATION

This is a non-provisional application of prior pending U.S. provisional application Ser. No. 60/286,278 filed on Apr. 25, 2001.

The present invention relates to a catalyst for the oxidation of alkanes, or a mixture of alkanes and alkenes, to their corresponding unsaturated carboxylic acids by vapor phase catalytic oxidation and, more particularly, to a method of making the catalyst and to a process for the vapor phase catalytic oxidation of alkanes, or a mixture of alkanes and alkenes, to their corresponding unsaturated carboxylic acids using a catalyst prepared by the present method of making a catalyst. The present invention also relates to a process for the vapor phase catalytic oxidation of alkanes, or a mixture of alkanes and alkenes, in the presence of ammonia, to their corresponding unsaturated nitriles using a catalyst prepared by the present method of making a catalyst.

Nitriles, such as acrylonitrile and methacrylonitrile, have been industrially produced as important intermediates for the preparation of fibers, synthetic resins, synthetic rubbers, and the like. The most popular method for producing such nitriles is to subject an olefin such presence of a catalyst at a high temperature. Known catalysts for conducting this reaction include a Mo—Bi—P—O catalyst, a V—Sb—O catalyst, an Sb—U—V—Ni—O catalyst, a Sb—Sn—O catalyst, a V—Sb—W—P—O catalyst and a catalyst obtained by mechanically mixing a V—Sb—W—O oxide and a Bi—Ce—Mo—W—O oxide. However, in view of the price difference between propane and propene or between isobutane and isobutene, attention has been drawn to the development of a method for producing acrylonitrile or methacrylonitrile by an ammoxidation reaction wherein a lower alkane, such as propane or isobutane, is used as a starting material, and it is catalytically reacted with ammonia and oxygen in a gaseous phase in the presence of a catalyst.

In particular, U.S. Pat. No. 5,281,745 discloses a method for producing an unsaturated nitrile comprising subjecting an alkane and ammonia in the gaseous state to catalytic oxidation in the presence of a catalyst which satisfies the conditions:

(1) the mixed metal oxide catalyst is represented by the empirical formula $$Mo_aV_bTe_cX_xO_n$$

wherein X is at least one element selected from the group consisting of niobium, tantalum, tungsten, titanium, aluminum, zirconium, chromium, manganese, iron, ruthenium, cobalt, rhodium, nickel, palladium, platinum, antimony, bismuth, boron and cerium and, when a=1, b=0.01 to 1.0, c=0.01 to 1.0, x=0.01 to 1.0 and n is a number such that the total valency of the metal elements is satisfied; and (2) the catalyst has X-ray diffraction peaks at the following angles (±0.3°) of 2θ in its X-ray diffraction pattern: 22.1°, 28.2°, 36.2°, 45.2° and 50.0°.

Similarly, Japanese Laid-Open Patent Application Publication No. 6-228073 discloses a method of nitrile preparation comprising reacting an alkane in a gas phase contact reaction with ammonia in the presence of a mixed metal oxide catalyst of the formula $$W_aV_bTe_cX_xO_n$$

wherein X represents one or more elements selected from niobium, tantalum, titanium, aluminum, zirconium, chromium, manganese, iron, ruthenium, cobalt, rhodium, nickel, palladium, platinum, antimony, bismuth, indium and cerium and, when a=1, b=0.01 to 1.0, c=0.01 to 1.0, x=0.01 to 1.0 and n is determined by the oxide form of the elements.

Unsaturated carboxylic acids such as acrylic acid and methacrylic acid are industrially important as starting materials for various synthetic resins, coating materials and plasticizers. Commercially, the current process for acrylic acid manufacture involves a two-step catalytic oxidation reaction starting with a propene feed. In the first stage, propene is converted to acrolein over a modified bismuth molybdate catalyst. In the second stage, acrolein product from the first stage is converted to acrylic acid using a catalyst composed of mainly molybdenum and vanadium oxides. In most cases, the catalyst formulations are proprietary to the catalyst supplier, but, the technology is well established. Moreover, there is an incentive to develop a single step process to prepare the unsaturated acid from its corresponding alkene. Therefore, the prior art describes cases where complex metal oxide catalysts are utilized for the preparation of unsaturated acid from a corresponding alkene in a single step.

Japanese Laid-Open Patent Application Publication No. 07-053448 discloses the manufacture of acrylic acid by the gas-phase catalytic oxidation of propene in the presence of mixed metal oxides containing Mo, V, Te, O and X wherein X is at least one of Nb, Ta, W, Ti, Al, Zr, Cr, Mn, Fe, Ru, Co, Rh, Ni, Pd, Pt, Sb, Bi, B, In, Li, Na, K, Rb, Cs and Ce.

Commercial incentives also exist for producing acrylic acid using a lower cost propane feed. Therefore, the prior art describes cases wherein a mixed metal oxide catalyst is used to convert propane to acrylic acid in one step.

U.S. Pat. No. 5,380,933 discloses a method for producing an unsaturated carboxylic acid comprising subjecting an alkane to a vapor phase catalytic oxidation reaction in the presence of a catalyst containing a mixed metal oxide comprising, as essential components, Mo, V, Te, O and X, wherein X is at least one element selected from the group consisting of niobium, tantalum, tungsten, titanium, aluminum, zirconium, chromium, manganese, iron, ruthenium, cobalt, rhodium, nickel, palladium, platinum, antimony, bismuth, boron, indium and cerium; and wherein the proportions of the respective essential components, based on the total amount of the essential components, exclusive of oxygen, satisfy the following relationships: 0.25<r(Mo)<0.98, 0.003<r(V)<0.5, 0.003<r(Te)<0.5 and 0.003<r(X)<0.5, wherein r(Mo), r(V), r(Te) and r(X) are the molar fractions of Mo, V, Te and X, respectively, based on the total amount of the essential components exclusive of oxygen.

Nonetheless, the prior art continues to seek ways to improve the performance of such mixed metal oxide catalysts. In particular, Japanese Laid-Open Pat. Application Publication No. 10-330343 discloses a single stage washing or a dual stage washing followed by calcination of a mixed metal oxide of the formula $$Mo_aV_bSb_cX_xO_n$$

wherein X is at least one metal element selected from Ti, Zr, Nb, Ta, Cr, W, Mn, Fe, Ru, Co, Rh, Ir, Ni, Pd, Pt, Cu, Ag, Zn, In, Sn, Pb, Bi, Ce and alkaline earth metals, wherein, when a=1, 0.02≦b≦0.99, 0.001≦c≦0.9, 0≦x≦0.89, 0.1≦c/b≦0.80 and n is a value determined by the oxidation state of the other elements, with solvents selected from aqueous oxalic acid, ethylene glycol or aqueous hydrogen peroxide. The so-formed catalyst is used for the ammoxidation of alkanes to form nitrites. Japanese Laid-Open Pat. Application Publication No. 11-043314 discloses the washing of a mixed metal oxide of the formula $$Mo_aV_bSb_cX_xO_n$$

wherein X is at least one metal element selected from Ti, Zr, Nb, Ta, Cr, W, Mn, Fe, Ru, Co, Rh, Ir, Ni, Pd, Pt, Cu, Ag, Zn, In, Sn, Pb, Bi, Ce and alkaline earth metals, where in, when a=1, $0.02 \leq b \leq 0.99$, $0.001 \leq c \leq 0.9$, $0 \leq x \leq 0.89$, $0.1 \leq c/b \leq 0.80$ and n is a value determined by the oxidation state of the other elements, with at least one solvent selected from an aqueous solution of an organic acid, an alcohol, an aqueous solution of an inorganic acid or an aqueous solution of hydrogen peroxide, followed by calcination. The so-formed material is indicated to be useful in such applications as electronic materials, electrode materials, mechanical inorganic materials and as catalysts in petrochemistry, etc. In particular, use as a catalyst in the oxidative dehydrogenation of ethane to produce ethylene is exemplified.

It has now been found that the performance of a mixed metal oxide catalyst having the empirical formula $$A_aV_bN_cX_dO_e$$

wherein

A is at least one element selected from the group consisting of Mo and W, N is at least one element selected from the group consisting of Te, Se and Sb, and X is at least one element selected from the group consisting of Nb, Ta, Ti, Al, Zr, Cr, Mn, Fe, Ru, Co, Rh, Ni, Pt, Bi, B, In, Ce, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu, wherein A, V, N and X are present in such amounts that the atomic ratio of A:V:N:X is a:b:c:d, and wherein, when a=1, b=0.01 to 2, c=0.01 to 1.0, d=0.01 to 1.0 and e is dependent on the oxidation state of the other elements, may be improved for the oxidation of an alkane, or a mixture of an alkane and an alkene, to an unsaturated carboxylic acid or may be improved for the ammoxidation of an alkane, or a mixture of an alkane and an alkene, to an unsaturated nitrile, by contacting the mixed metal oxide catalyst with a liquid contact member selected from the group consisting of organic acids, alcohols, inorganic acids and hydrogen peroxide, recovering insoluble material from such contacting, followed by calcination of recovered insoluble materials in a non-oxidizing atmosphere and then promoting the so-formed catalyst with a promoter.

Thus, in a first aspect, the present invention provides a process for preparing an improved catalyst, said process comprising:

(a) providing a mixed metal oxide having the empirical formula $$A_aV_bN_cX_dO_e$$

wherein A is at least one element selected from the group consisting of Mo and W, N is at least one element selected from the group consisting of Te, Sb and Se, and X is at least one element selected from the group consisting of Nb, Ta, Ti, Al, Zr, Cr, Mn, Fe, Ru, Co, Rh, Ni, Pt, Bi, B, In, Ce, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu, wherein A, V, N and X are present in such amounts that the atomic ratio of A:V:N:X is a:b:c:d, and wherein, when a=1, b=0.01 to 2, c=0.01 to 1, d=0.01 to 1 and e is dependent on the oxidation state of the other elements;

(b) contacting said mixed metal oxide with a liquid contact member selected from the group consisting of organic acids, alcohols, inorganic acids and hydrogen peroxide to form a contact mixture;

(c) recovering insoluble material from said contact mixture; and (d) calcining said recovered insoluble material in a non-oxidizing atmosphere:

(e) admixing said calcined recovered insoluble material with (i) at least one promoter element or compound thereof, wherein said at least one promoter element is selected from the group consisting of Au, Ag, Re, Pr, Zn, Ga, Pd, Ir, Nd, Y, Sm, Tb, Br, Cu, Sc, Cl, F and I, and (ii) at least one solvent for said at least one promoter element or compound thereof to form an admixture;

(f) removing said at least one solvent from said so-formed admixture to form a catalyst precursor;

(g) calcining said catalyst precursor.

In a second aspect, the present invention provides a further process for preparing an improved catalyst, said process comprising:

(a) providing a mixed metal oxide having the empirical formula $$A_aV_bN_cX_dO_e$$

wherein A is at least one element selected from the group consisting of Mo and W, N is at least one element selected from the group consisting of Te, Sb and Se, and X is at least one element selected from the group consisting of Nb, Ta, Ti, Al, Zr, Cr, Mn, Fe, Ru, Co, Rh, Ni, Pt, Bi, B, In, Ce, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu, wherein A, V, N and X are present in such amounts that the atomic ratio of A:V:N:X is a:b:c:d, and wherein, when a=1, b=0.01 to 2, c=0.01 to 1, d=0.01 to 1 and e is dependent on the oxidation state of the other elements;

(b) contacting said mixed metal oxide with a liquid contact member selected from the group consisting of organic acids, alcohols, inorganic acids and hydrogen peroxide to form a contact mixture;

(c) recovering insoluble material from said contact mixture; and (d) calcining said recovered insoluble material in a non-oxidizing atmosphere in the presence of a source of halogen.

In a third aspect, the present invention provides a still further process for preparing an improved catalyst, said process comprising:

a) providing a mixed metal oxide having the empirical formula $$A_aV_bN_cX_dO_e$$

wherein A is at least one element selected from the group consisting of Mo and W, N is at least one element selected from the group consisting of Te, Sb and Se, and X is at least one element selected from the group consisting of Nb, Ta, Ti, Al, Zr, Cr, Mn, Fe, Ru, Co, Rh, Ni, Pt, Bi, B, In, Ce, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu, wherein A, V, N and X are present in such amounts that the atomic ratio of A:V:N:X is a:b:c:d, and wherein, when a=1, b=0.01 to 2, c=0.01 to 1, d=0.01 to 1 and e is dependent on the oxidation state of the other elements;

(b) contacting said mixed metal oxide with a liquid contact member selected from the group consisting of organic acids, alcohols, inorganic acids and hydrogen peroxide to form a contact mixture;

(c) recovering insoluble material from said contact mixture;

(d) calcining said recovered insoluble material in a non-oxidizing atmosphere to form a calcined recovered insoluble material; and (e) contacting said calcined recovered insoluble material with a source of halogen.

In fourth, fifth and sixth aspects, the present invention provides catalysts produced by the processes according to the first, second and third aspects of the invention, respectively.

In seventh, eighth and ninth aspects, the present invention provides processes for producing an unsaturated carboxylic acid which comprise subjecting an alkane, or a mixture of an alkane and an alkene, to a vapor phase catalytic oxidation reaction in the presence of a catalyst produced by the processes according to the first, second and third aspects of the invention, respectively.

In tenth, eleventh and twelfth aspects, the present invention provides processes for producing an unsaturated nitrile which comprise subjecting an alkane, or a mixture of an alkane and an alkene, and ammonia to a vapor phase catalytic oxidation reaction in the presence of a catalyst produced by the processes according to the first, second and third aspects of the invention, respectively.

The mixed metal oxide, which is used as the starting material for the present process of preparing an improved catalyst, is a mixed metal oxide that includes a material having the empirical formula

wherein A is at least one element selected from the group consisting of Mo and W, N is at least one element selected from the group consisting of Te, Sb and Se, and X is at least one element selected from the group consisting of Nb, Ta, Ti, Al, Zr, Cr, Mn, Fe, Ru, Co, Rh, Ni, Pt, Sb, Bi, B, In, Ce, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu; and wherein, when a=1, b=0.01 to 2, c=0.01 to 1.0, d=0.01 to 0.1 and e is dependent oxidation state of the other elements.

Preferably, when a=1, b=0.1 to 0.5, c=0.05 to 0.5 and d=0.01 to 0.5. More preferably, when a=1, b=0.15 to 0.45, c=0.05 to 0.45 and d=0.01 to 0.1. The value of e, i.e. the amount of oxygen present, is dependent on the oxidation state of the other elements in the catalyst. However, e is typically in the range of from 3 to 4.7.

For example, such a mixed metal oxide may be prepared by:

admixing compounds of elements A, V, N, X and at least one solvent to form a mixture, wherein A is at least one element selected from the group consisting of Mo and W, N is at least one element selected from the group consisting of Te, Sb and Se, and X is at least one element selected from the group consisting of Nb, Ta, Ti, Al, Zr, Cr, Mn, Fe, Ru, Co, Rh, Ni, Pt, Bi, B, In, Ce, As, Ge, Sn, Li, Na, K, Rb, Cs, Fr, Be, Mg, Ca, Sr, Ba, Hf, Pb, P, Pm, Eu, Gd, Dy, Ho, Er, Tm, Yb and Lu, wherein A, V, N and X are present in such amounts that the atomic ratio of A:V:N:X is a:b:c:d, and wherein, when a=1, b=0.01 to 2, c=0.01 to 1.0 and d=0.01 to 1.0;

removing the at least one solvent from the mixture to form a precursor; and calcining the precursor to form a mixed metal oxide.

Preferred mixed metal oxides have the empirical formulae $Mo_aV_bTe_cNb_dO_e$ and $W_aV_bTe_cNb_dO_e$ wherein a, b, c, d and e are as previously defined.

The mixed metal oxide to be used as the starting material may be an orthorhombic phase material.

In such a case, the orthorhombic phase mixed metal oxide may be prepared, for example, by the process comprising:

(a) providing a mixed metal oxide having the empirical formula

wherein A is at least one element selected from the group consisting of Mo and W, N is at least one element selected from the group consisting of Te, Sb and Se, and X is at least one element selected from the group consisting of Nb, Ta, Ti, Al, Zr, Cr, Mn, Fe, Ru, Co, Rh, Ni, Pt, Bi, B, In, Ce, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu, wherein A, V, N and X are present in such amounts that the atomic ratio of A:V:N:X is a:b:c:d, and wherein, when a=1, b=0.01 to 2, c=0.01 to 1, d=0.01 to 1 and e is dependent on the oxidation state of the other elements;

(b) contacting said mixed metal oxide with a liquid contact member selected from the group consisting of organic acids, alcohols, inorganic acids and hydrogen peroxide to form a contact mixture; and (c) recovering insoluble material from said contact mixture to obtain said orthorhombic phase mixed metal oxide.

Alternatively, such an orthorhombic phase mixed metal oxide may be prepared, for example, by a process comprising:

(a) admixing compounds of elements A, V, N and X and at least one solvent to form a solution, wherein A is at least one element selected from the group consisting of Mo and W, N is at least one element selected from the group consisting of Te, Sb and Se, and X is at least one element selected from the group consisting of Nb, Ta, Ti, Al, Zr, Cr, Mn, Fe, Ru, Co, Rh, Ni, Pt, Bi, B, In, Ce, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu, wherein A, V, N and X are present in such amounts that the atomic ratio of A:V:N:X is a:b:c:d, and wherein, when a=1, b=0.01 to 2, c=0.01 to 1.0 and d=0.01 to 1.0;

(b) admixing a seeding effective amount of an orthorhombic phase mixed metal oxide seed, substantially free of hexagonal phase mixed metal oxide, with said solution to form a seeded solution;

(c) removing said at least one solvent from said seeded solution to form a catalyst precursor; and (d) calcining said catalyst precursor to obtain said orthorhombic phase mixed metal oxide.

By a seeding effective amount is meant an amount of seed material effective to cause nucleation of the orthorhombic phase, e.g., 0.01% by weight of seed material based on the total weight of the solution being seeded. By an orthorhombic phase mixed metal oxide which is substantially free of hexagonal phase mixed metal oxide is meant a material that contains not less than 90% by weight of orthorhombic phase based on the total weight of the material.

The orthorhombic phase mixed metal oxide substantially free of hexagonal phase mixed metal oxide, to be used as seed, may be prepared, for example, by:

taking a mixed metal oxide having the empirical formula

$A_a V_b N_c X_d O_e$ wherein A is at least one element selected from the group consisting of Mo and W, N is at least one element selected from the group consisting of Te, Sb and Se, and X is at least one element selected from the group consisting of Nb, Ta, Ti, Al, Zr, Cr, Mn, Fe, Ru, Co, Rh, Ni, Pt, Bi, B, In, Ce, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu, wherein, when a=1, b=0.01 to 2, c=0.01 to 1.0, d=0.01 to 1.0 and e is dependent on the oxidation state of the other elements;

contacting the mixed metal oxide with a liquid contacting member selected from the group consisting of organic acids, alcohols, inorganic acids and hydrogen peroxide to form a contact mixture; and recovering insoluble material, to be used as seed material, from the contact mixture.

Alternatively, the orthorhombic phase mixed metal oxide substantially free of hexagonal phase mixed metal oxide, to be used as seed, may be prepared, for example, by:

admixing compounds of elements A, V, N and X and at least one solvent to form a mixture wherein A is at least one element selected from the group consisting of Mo and W, N is at least one element selected from the group consisting of Te, Sb and Se, and X is at least one element selected from the group consisting of Nb, Ta, Ti, Al, Zr, Cr, Mn, Fe, Ru, Co, Rh, Ni, Pt, Bi, B, In, Ce, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu, wherein A, V, N and X are present in such amounts that the atomic ratio of A:V:N:X is a:b:c:d, and wherein, when a=1, b=0.01 to 2, c=0.01 to 1.0 and d=0.01 to 1.0;

removing the at least one solvent from the mixture to form a precursor;

calcining the precursor to form a calcined precursor;

contacting the calcined precursor with a liquid contact member selected from the group consisting of organic acids, alcohols, inorganic acids and hydrogen peroxide to form a contact mixture; and recovering insoluble material, to be used as seed material, from the contact mixture.

Suitable solvents, for the above-noted processes, include water; alcohols including, but not limited to, methanol, ethanol, propanol, and diols, etc.; as well as other polar solvents known in the art. Generally, water is preferred. The water is any water suitable for use in chemical syntheses including, without limitation, distilled water and de-ionized water. The amount of water present is preferably an amount sufficient to keep the elements substantially in solution long enough to avoid or minimize compositional and/or phase segregation during the preparation steps. Accordingly, the amount of water will vary according to the amounts and solubilities of the materials combined. However, the amount of water is preferably sufficient to ensure an aqueous solution is formed, at the time of mixing.

The solvent is removed by any suitable method, known in the art, to form a catalyst precursor. Such methods include, without limitation, vacuum drying, freeze drying, spray drying, rotary evaporation and air drying.

For example, in the case of water being the solvent: Vacuum drying is generally performed at pressures ranging from 10 mmHg to 500 mmHg. Freeze drying typically entails freezing the solution, using, for instance, liquid nitrogen, and drying the frozen solution under vacuum. Spray drying is generally performed under an inert atmosphere such as nitrogen or argon, with an inlet temperature ranging from 125° C. to 200° C. and an outlet temperature ranging from 75° C. to 150° C. Rotary evaporation is generally performed at a bath temperature of from 25° C. to 90° C. and at a pressure of from 10 mmHg to 760 mmHg, preferably at a bath temperature of from 40° to 90° C. and at a pressure of from 10 mmHg to 350 mmHg, more preferably at a bath temperature of from 40° C. to 60° C. and at a pressure of from 10 mmHg to 40 mmHg. Air drying may be effected at temperatures ranging from 25° C. to 90° C. Rotary evaporation or air drying are generally preferred.

Contacting with a liquid contact member selected from the group consisting of organic acids, alcohols, inorganic acids and hydrogen peroxide (whether it be for the purpose of making the final catalyst, an orthorhombic phase mixed metal oxide, or for the purpose of making a seed material) may be effected without any particular restrictions (so long as, in the case of the preparation of the orthorhombic phase mixed metal oxide, the hexagonal phase is fully removed from the mixed metal oxide or the calcined precursor). In this regard, the liquid contact member is normally used in an amount of 1 to 100 times the volume of the mixed metal oxide or the first calcined precursor, preferably 3 to 50 times the volume, more preferably 5 to 25 times the volume. (Contacting at elevated temperatures will remove the hexagonal phase more rapidly. However, if prolonged contact time is not a consideration, contacting at room temperature may be utilized.) Normally, contact temperatures of room temperature to 100° C. are utilized, preferably 50° C. to 90° C., more preferably 60° C. to 80° C. As previously noted, contact time will be affected by the temperature at which the contacting is carried out. Normally, contact times of 1 to 100 hours are utilized, preferably 2 to 20 hours, more preferably 5 to 10 hours. The contact mixture is preferably agitated during the contacting.

There are no particular restrictions upon the organic acids which may be used as the liquid contacting member. For example, oxalic acid, formic acid, acetic acid, citric acid and tartaric acid may be used, however, oxalic acid is preferred. If the organic acid is a liquid, it may be used as is or in an aqueous solution. If the organic acid is a solid, it is used in an aqueous solution. When using aqueous solutions, there are no particular restrictions on the concentration of the organic acid. Normally, the concentration of the organic acid in the aqueous solution can vary from 0.1 to 50% by weight, preferably 1 to 15% by weight.

There are no particular restrictions upon the alcohols which may be used as the liquid contacting member. For example, methanol, ethanol, propanol, butanol, hexanol and diols may be utilized, however, alcohols having one to four carbon atoms are preferred, with ethylene glycol being particularly preferred. The alcohols may be utilized in the form of aqueous solutions, but, if so, the water content should be held to 20% by weight or less for the best effectiveness.

Similarly, there are no particular restrictions upon the inorganic acids which may be used as the liquid contacting member. For example, telluric acid, nitric acid, sulfuric acid, phosphoric acid, hydrochloric acid, perchloric acid, chloric acid and hypochlorous acid may be used. The inorganic acids are typically used as aqueous solutions with concentrations of the acids in the range of from 0.1 to 50% by weight, preferably from 0.1 to 10% by weight.

When hydrogen peroxide is utilized as the liquid contacting member, it is used in the form of an aqueous solution having a concentration in the range of from 0.1 to 50% by weight, preferably from 1 to 10% by weight.

After contacting with the liquid contacting member, insoluble material is recovered from the so-formed contact mixture. The insoluble material may be recovered by any conventional method, e.g., centrifugation or filtration. If the contacting was conducted at elevated temperature, the contact mixture may be cooled prior to recovery of the insoluble material. If desired, the recovered insoluble material may be washed with one of the previously disclosed solvents, preferably water.

Calcination may be conducted in an oxidizing atmosphere, e.g., in air, oxygen-enriched air or oxygen, or in the substantial absence of oxygen, e.g., in an inert atmosphere or in vacuo. The inert atmosphere may be any material which is substantially inert, i.e., does not react or interact with, the catalyst precursor. Suitable examples include, without limitation, nitrogen, argon, xenon, helium or mixtures thereof. Preferably, the inert atmosphere is argon or nitrogen, more preferably argon. The inert atmosphere may flow over the surface of the catalyst precursor or may not flow thereover (a static environment). When the inert atmosphere does flow over the surface of the catalyst precursor, the flow rate can vary over a wide range, e.g., at a space velocity of from 1 to 500 $hr^{-1}$.

The calcination is usually performed at a temperature of from 350° C. to 850° C., preferably from 400° C. to 700° C., more preferably from 500° C. to 640° C. The calcination is performed for an amount of time suitable to form the aforementioned catalyst. Typically, the calcination is performed for from 0.5 to 30 hours, preferably from 1 to 25 hours, more preferably for from 1 to 15 hours, to obtain the desired promoted mixed metal oxide.

In a preferred mode of operation, calcination is conducted in two stages. In the first stage, the catalyst precursor is calcined in an oxidizing environment (e.g. air) at a temperature of from 200° C. to 400° C., preferably from 275° C. to 325° C. for from 15 minutes to 8 preferably for from 1 to 3 hours. In the second stage, the material from the first stage is calcined in a non-oxidizing environment (e.g., an inert atmosphere) at a temperature of from 500° C. to 750° C., preferably for from 550° C. to 650° C., for 15 minutes to 8 hours, for from 1 to 3 hours. Optionally, a reducing gas, such as, for example, ammonia or hydrogen, may be added during the second stage calcination.

In a particularly preferred mode of operation, in the first stage, the material to be calcined is placed in the desired oxidizing atmosphere at room temperature and then raised to the first stage calcination temperature and held there for the desired first stage calcination time. The atmosphere is then replaced with the desired non-oxidizing atmosphere for the second stage calcination, the temperature is raised to the desired second stage calcination temperature and held there for the desired second stage calcination time.

In an another preferred mode of operation, the insoluble material recovered from the contact mixture is calcined in a non-oxidizing atmosphere, preferably an inert atmosphere. In the case where the promoter element is a halogen, such halogen may be added to the aforementioned non-oxidizing atmosphere.

Although any type of heating mechanism, e.g., a furnace, may be utilized during the calcination, it is preferred to conduct the calcination under a flow of the designated gaseous environment. Therefore, it is advantageous to conduct the calcination in a bed with continuous flow of the desired gas(es) through the bed of solid catalyst precursor particles.

When the present invention requires calcination in a non-oxidizing atmosphere, the calcination is conducted in an inert atmosphere or in vacuo, preferably, in an inert atmosphere. The inert atmosphere may be any material which is substantially inert to, i.e. does not react or interact with, the material being calcined. Suitable examples include, without limitation, nitrogen, argon, xenon, helium or mixtures thereof. Preferably the inert gas is argon or nitrogen. Preferably, the inert atmosphere flows over the surface of the material to be calcined. While the flow rate may vary over a wide range, typically, a space velocity of from 1 to 500 $hr^{-1}$ may be utilized. The calcination in a non-oxidizing atmosphere is usually performed at a temperature of from 350° C. to 850° C., preferably from 400° C. to 700° C., more preferably from 500° C. to 640° C. The calcination in a non-oxidizing atmosphere is typically performed for from 0.5 to 20 hours, preferably for from 1 to 10 hours, more preferably for from 1 to 5 hours. In the calcination in a non-oxidizing atmosphere, the material to be calcined is preferably placed under the inert atmosphere at room temperature, then raised to the desired calcination temperature while under the inert atmosphere, and then maintained at the desired calcination temperature for the desired time of calcination. Typically, after calcination the calcined material is allowed to cool while being maintained under the inert atmosphere.

The starting materials for the above mixed metal oxide are not particularly limited. A wide range of materials including, for example, oxides, nitrates, halides or oxyhalides, alkoxides, acetylacetonates, and organometallic compounds may be used. For example, ammonium heptamolybdate may be utilized for the source of molybdenum in the catalyst. However, compounds such as $MoO_3$, $MoO_2$, $MoCl_5$, $MoOCl_4$, $Mo(OC_2H_5)_5$, molybdenum acetylacetonate, phosphomolybdic acid and silicomolybdic acid may also be utilized instead of ammonium heptamolybdate. Similarly, ammonium metavanadate may be utilized for the source of vanadium in the catalyst. However, compounds such as $V_2O_5$, $V_2O_3$, $VOCl_3$, $VCl_4$, $VO(OC_2H_5)_3$, vanadium acetylacetonate and vanadyl acetylacetonate may also be utilized instead of ammonium metavanadate. The tellurium source may include telluric acid, $TeCl_4$, $Te(OC_2H_5)_5$, $Te(OCH(CH_3)_2)_4$ and $TeO_2$. The niobium source may include ammonium niobium oxalate, $Nb_2O_5$, $NbCl_5$, niobic acid or $Nb(OC_2H_5)_5$ as well as the more conventional niobium oxalate.

With respect to the promoter elements or compounds thereof that may be utilized to make the improved catalysts of the present invention, no particular restrictions are placed thereon. With this in mind, the following lists are merely illustrative of available sources of these elements or the compounds thereof, not limiting thereon.

The gold source may be ammonium tetrachloroaurate, gold bromide, gold chloride, gold cyanide, gold hydroxide, gold iodide, gold oxide, gold trichloride acid or gold sulfide.

The silver source may be silver acetate, silver acetylacetonate, silver benzoate, silver bromide, silver carbonate, silver chloride, silver citrate hydrate, silver fluoride, silver iodide, silver lactate, silver nitrate, solver nitrite, silver oxide, silver phosphate, or a solution of silver in an aqueous inorganic acid, e.g., nitric acid.

The copper source may be copper acetate, copper acetate monohydrate, copper acetate hydrate, copper acetylacetonate, copper bromide, copper carbonate, copper chloride, copper chloride dihydrate, copper fluoride, copper formate hydrate, copper gluconate, copper hydroxide, copper iodide, copper methoxide, copper nitrate hydrate, copper nitrate, copper oxide, copper tartrate hydrate, or a solution of copper in an aqueous inorganic acid, e.g., nitric acid.

The praseodymium source may be praseodymium (III) acetate, praseodymium (III) acetylacetonate, praseodymium (III) bromide, praseodymium (III) carbonate, praseodymium (III) chloride, praseodymium (III) fluoride, praseodymium (III) hexafluoroacetylacetonate, praseodymium (III) iodide, praseodymium (III) isopropoxide, praseodymium (III) nitrate, praseodymium (III) oxalate, praseodymium (III) oxide, praseodymium (III) perchlorate, praseodymium (III) sulfate, praseodymium (III) triflate or praseodymium (III) trifluoromethane sulfate.

The terbium source may be a solution of terbium in an aqueous inorganic acid, e.g., nitric acid.

The neodymium source may be a neodymium salt, e.g., neodymium nitrate, dissolved in an aqueous inorganic acid, e.g. nitric acid.

The yittrium source may be an yittrium salt, e.g., yittrium nitrate, dissolved in water.

The scandium source may be scandium acetate, scandium bromide hydrate, scandium chloride, scandium chloride hexahydrate, scandium chloride hydrate, scandium fluoride, scandium iodide, scandium isopropoxide, scandium nitrate hydrate, scandium oxalate hydrate, scandium oxide, or a solution of scandium in an aqueous inorganic acid, e.g., nitric acid.

The rhenium source may be ammonium perrhenate, rhenium carbonyl, rhenium chloride, rhenium fluoride, rhenium oxide, rhenium pentacarbonyl bromide, rhenium pentacarbonyl chloride and rhenium sulfide.

The palladium source may be palladium nitrate, palladium (II) acetate, palladium oxalate, palladium oxide, palladium hydroxide, palladium chloride, palladium acetylacetonate or palladium metal.

The iridium source may be iridium acetylacetonate, iridium bromide hydrate, iridium chloride, iridium chloride hydrochloride hydrate, iridium chloride hydrate, iridium oxide, iridium oxide hydrate, iridium oxoacetate trihydrate or iridium dissolved in an aqueous inorganic acid, e.g., nitric acid.

The samarium source may be samarium (III) acetate hydrate, samarium (III) acetylacetonate hydrate, samarium (II) bromide, samarium (III) bromide, samarium (III) bromide hexahydrate, samarium (III) carbonate hydrate, samarium (II) chloride, samarium (III) chloride, samarium (III) chloride hexahydrate, samarium (III) fluoride, samarium (II) iodide, samarium (III) iodide, samarium (III) isopropoxide, samarium (III) nitrate hexahydrate, samarium (III) oxalate hydrate, samarium (III) oxide or a solution of samarium in an aqueous inorganic acid, e.g., nitric acid.

The zinc source may be zinc acetate, zinc acetylacetonate, zinc acrylate, zinc bis(2,2,6,6-tetramethyl-3,5-heptanedioate), zinc bromide, zinc carbonate hydroxide, zinc chloride, zinc citrate, zinc cyclohexanebutyrate, zinc 3,5-di-tert-butylsalicylate, zinc fluoride, zinc iodide, zinc L-lactate, zinc methacrylate, zinc nitrate, zinc oxide, zinc perchlorate or zinc stearate.

The gallium source may be $Ga_2O$, $GaCl_3$, $GaCl_2$, gallium acetylacetonate, $Ga_2O_3$ or $Ga(NO_3)_3$.

The bromine source may be added as one of the above reagents as a bromide, e.g., as the bromide salt of X (where X is at least one element selected from the group consisting of Nb. Ta, Ti, Al, Zr, Cr, Mn, Fe, Ru, Co, Rh, Ni, Pt, Sb, Bi, B, In, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu), for example, as molybdenum bromide, tellurium tetrabromide, niobium bromide or vanadium bromide; or as a solution of bromine in an aqueous inorganic acid, e.g., nitric acid. The bromine source may also be added during the calcination of the recovered insoluble material or, after calcination, as a bromine treatment step. For example, the bromine source may be added to the calcination atmosphere or to the oxidation or ammoxidation reactor feed stream, as, for example, HBr, $Br_2$, ethyl bromide or the like, to achieve a promotional effect with the bromine.

The chlorine source may also be added as one of the above reagents as a chloride, e.g., as the chloride salt of X (where X is at least one element selected from the group consisting of Nb, Ta, Ti, Al, Zr, Cr, Mn, Fe, Ru, Co, Rh, Ni, Pt, Sb, Bi, B, In, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu), for example, as molybdenum chloride, tellurium tetrachloride, niobium chloride or vanadium chloride. The chlorine source may also be added during the calcination of the recovered insoluble material or, after calcination, as a chlorine treatment step. For example, the chlorine source may be added to the calcination atmosphere or to the oxidation or ammoxidation reactor feed stream, as, for example, HCl, $Cl_2$, ethyl chloride or the like, to achieve a promotional effect with the chloride.

The fluorine source may be added as one of the above reagents as a fluoride, e.g., as the fluoride salt of X (where X is at least one element selected from the group consisting of Nb, Ta, Ti, Al, Zr, Cr, Mn, Fe, Ru, Co, Rh, Ni, Pt, Sb, Bi, B, In, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu), for example, as molybdenum fluoride, tellurium fluoride, niobium fluoride or vanadium fluoride. The fluorine source may also be added during the calcination of the recovered insoluble material or, after calcination, as a fluorine treatment step. For example, the fluorine source may be added to the calcination atmosphere or to the oxidation or ammoxidation reactor feed stream, as, for example, HF, $F_2$, ethyl fluoride or the like, to achieve a promotional effect with the fluoride.

The iodine source may be added as one of the above reagents as a fluoride, e.g., as the fluoride salt of X (where X is at least one element selected from the group consisting of Nb, Ta, Ti, Al, Zr, Cr, Mn, Fe, Ru, Co, Rh, Ni, Pt, Sb, Bi, B, In, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu), for example, as molybdenum iodide, tellurium iodide, niobium iodide or vanadium iodide. The iodine source may also be added during the calcination of the recovered insoluble material or, after calcination, as an iodine treatment step. For example, the iodine source may be added to the calcination atmosphere or to the oxidation or ammoxidation reactor feed stream, as, for example, HI, $I_2$, ethyl iodide or the like, to achieve a promotional effect with the iodide.

The promoter element(s) or the compounds thereof are added in amounts so as to achieve a level of promoter element in the improved catalyst such that the atomic ratio of promoter element: element(s) A is 0.001 to 1:1, preferably 0.001 to 0.1:1.

The improved catalyst formed by the aforementioned techniques, exhibits excellent catalytic activities by itself. However, the mixed metal oxide may be converted to a catalyst having higher activities by grinding.

There is no particular restriction as to the grinding method, and conventional methods may be employed. As a dry grinding method, a method of using a gas stream grinder may, for example, be mentioned wherein coarse particles are permitted to collide with one another in a high speed gas stream for grinding. The grinding may be conducted not only mechanically but also by using a mortar or the like in the case of a small scale operation.

As a wet grinding method wherein grinding is conducted in a wet state by adding water or an organic solvent to the above mixed metal oxide, a conventional method of using a rotary cylinder-type medium mill or a medium-stirring type mill, may be mentioned. The rotary cylinder-type medium mill is a wet mill of the type wherein a container for the object to be ground is rotated, and it includes, for example, a ball mill and a rod mill. The medium-stirring type mill is a wet mill of the type wherein the object to be ground, contained in a container is stirred by a stirring apparatus, and it includes, for example, a rotary screw type mill, and a rotary disc type mill.

The conditions for grinding may suitably be set to meet the nature of the above-mentioned promoted mixed metal oxide, the viscosity, the concentration, etc. of the solvent used in the case of wet grinding, or the optimum conditions of the grinding apparatus. However, it is preferred that grinding is conducted until the average particle size of the ground catalyst precursor would usually be at most 20 $\mu$m, more preferably at most 5 $\mu$m. Improvement in the catalytic performance may occur due to such grinding.

Further, in some cases, it is possible to further improve the catalytic activities by further adding a solvent to the ground catalyst precursor to form a solution or slurry, followed by drying again. There is no particular restriction as to the concentration of the solution or slurry, and it is usual to adjust the solution or slurry so that the total amount of the starting material compounds for the ground catalyst precursor is from 10 to 60 wt %. Then, this solution or slurry is dried by a method such as spray drying, freeze drying, evaporation to dryness or vacuum drying, preferably by the spray drying method. Further, similar drying may be conducted also in the case where wet grinding is conducted.

The oxide obtained by the above-mentioned method may be used as a final catalyst, but it may further be subjected to heat treatment usually at a temperature of from 200° to 700° C. for from 0.1 to 10 hours.

The mixed metal oxide thus obtained may be used by itself as a solid catalyst, but may be formed into a catalyst together with a suitable carrier such as silica, alumina, titania, aluminosilicate, diatomaceous earth or zirconia. Further, it may be molded into a suitable shape and particle size depending upon the scale or system of the reactor.

In its seventh, eighth and ninth aspects, the present invention provides processes for producing an unsaturated carboxylic acid, which comprise subjecting an alkane, or a mixture of an alkane and an alkene, to a vapor phase catalytic oxidation reaction in the presence of a catalyst produced in accord with the present invention to produce an unsaturated carboxylic acid.

In the production of such an unsaturated carboxylic acid, it is preferred to employ a starting material gas which contains steam. In such a case, as a starting material gas to be supplied to the reaction system, a gas mixture comprising a steam-containing alkane, or a steam-containing mixture of alkane and alkene, and an oxygen-containing gas, is usually used. However, the steam-containing alkane, or the steam-containing mixture of alkane and alkene, and the oxygen-containing gas may be alternately supplied to the reaction system. The steam to be employed may be present in the form of steam gas in the reaction system, and the manner of its introduction is not particularly limited.

In regard to the use of a halogen as the promoter element of the catalyst of the present invention, it is possible to add a gaseous halogen source as previously identified to the gas feed to the reaction.

Further, as a diluting gas, an inert gas such as nitrogen, argon or helium may be supplied. The molar ratio (alkane or mixture of alkane and alkene):(oxygen):(diluting gas): ($H_2O$) in the starting material gas is preferably (1):(0.1 to 10):(0 to 20):(0.2 to 70), more preferably (1):(1 to 5.0):(0 to 10):(5 to 40).

When steam is supplied together with the alkane, or the mixture of alkane and alkene, as starting material gas, the selectivity for an unsaturated carboxylic acid is distinctly improved, and the unsaturated carboxylic acid can be obtained from the alkane, or mixture of alkane and alkene, in good yield simply by contacting in one stage. However, the conventional technique utilizes a diluting gas such as nitrogen, argon or helium for the purpose of diluting the starting material. As such a diluting gas, to adjust the space velocity, the oxygen partial pressure and the steam partial pressure, an inert gas such as nitrogen, argon or helium may be used together with the steam.

As the starting material alkane it is preferred to employ a $C_{3-8}$alkane, particularly propane, isobutane or n-butane; more preferably, propane or isobutane; most preferably, propane. According to the present invention, from such an alkane, an unsaturated carboxylic acid such as an $\alpha,\beta$-unsaturated carboxylic acid can be obtained in good yield. For example, when propane or isobutane is used as the starting material alkane, acrylic acid or methacrylic acid will be obtained, respectively, in good yield.

In the present invention, as the starting material mixture of alkane and alkene, it is possible to employ a mixture of $C_{3-8}$alkane and $C_{3-8}$alkene, particularly propane and propene, isobutane and isobutene or n-butane and n-butene. As the starting material mixture of alkane and alkene, propane and propene or isobutane and isobutene are more preferred. Most preferred is a mixture of propane and propene. According to the present invention, from such a mixture of an alkane and an alkene, an unsaturated carboxylic acid such as an $\alpha,\beta$-unsaturated carboxylic acid can be obtained in good yield. For example, when propane and propene or isobutane and isobutene are used as the starting material mixture of alkane and alkene, acrylic acid or methacrylic acid will be obtained, respectively, in good yield. Preferably, in the mixture of alkane and alkene, the alkene is present in an amount of at least 0.5% by weight, more preferably at least 1.0% by weight to 95% by weight; most preferably, 3% by weight to 90% by weight.

As an alternative, an alkanol, such as isobutanol, which will dehydrate under the reaction conditions to form its corresponding alkene, i.e. isobutene, may also be used as a feed to the present process or in conjunction with the previously mentioned feed streams.

The purity of the starting material alkane is not particularly limited, and an alkane containing a lower alkane such as methane or ethane, air or carbon dioxide, as impurities, may be used without any particular problem. Further, the starting material alkane may be a mixture of various alkanes. Similarly, the purity of the starting material mixture of alkane and alkene is not particularly limited, and a mixture of alkane and alkene containing a lower alkene such as ethene, a lower alkane such as methane or ethane, air or carbon dioxide, as impurities, may be used without any particular problem. Further, the starting material mixture of alkane and alkene may be a mixture of various alkanes and alkenes.

There is no limitation on the source of the alkene. It may be purchased, per se, or in admixture with an alkane and/or other impurities. Alternatively, it can be obtained as a by-product of alkane oxidation. Similarly, there is no limitation on the source of the alkane. It may be purchased, per se, or in admixture with an alkene and/or other impurities. Moreover, the alkane, regardless of source, and the alkene, regardless of source, may be blended as desired.

The detailed mechanism of the oxidation reaction of the present invention is not clearly understood, but the oxidation reaction is carried out by oxygen atoms present in the above promoted mixed metal oxide or by molecular oxygen present in the feed gas. To incorporate molecular oxygen into the feed gas, such molecular oxygen may be pure oxygen gas. However, it is usually more economical to use an oxygen-containing gas such as air, since purity is not particularly required.

It is also possible to use only an alkane, or a mixture of alkane and alkene, substantially in the absence of molecular oxygen for the vapor phase catalytic reaction. In such a case, it is preferred to adopt a method wherein a part of the catalyst is appropriately withdrawn from the reaction zone from time to time, then sent to an oxidation regenerator, regenerated and then returned to the reaction zone for reuse. As the regeneration method of the catalyst, a method may, for example, be mentioned which comprises contacting an oxidative gas such as oxygen, air or nitrogen monoxide with the catalyst in the regenerator usually at a temperature of from 300° to 600° C.

These aspects of the present invention will be described in further detail with respect to a case where propane is used as the starting material alkane and air is used as the oxygen source. The reaction system may be a fixed bed system or a fluidized bed system. However, since the reaction is an exothermic reaction, a fluidized bed system may preferably be employed whereby it is easy to control the reaction temperature. The proportion of air to be supplied to the reaction system is important for the selectivity for the resulting acrylic acid, and it is usually at most 25 moles, preferably from 0.2 to 18 moles per mole of propane, whereby high selectivity for acrylic acid can be obtained. This reaction can be conducted usually under atmospheric pressure, but may be conducted under a slightly elevated pressure or slightly reduced pressure. With respect to other alkanes such as isobutane, or to mixtures of alkanes and alkenes such as propane and propene, the composition of the feed gas may be selected in accordance with the conditions for propane.

Typical reaction conditions for the oxidation of propane or isobutane to acrylic acid or methacrylic acid may be utilized in the practice of the present invention. The process may be practiced in a single pass mode (only fresh feed is fed to the reactor) or in a recycle mode (at least a portion of the reactor effluent is returned to the reactor). General conditions for the process of the present invention are as follows: the reaction temperature can vary from 200° C. to 700° C., but is usually in the range of from 200° C. to 550° C., more preferably 250° C. to 480° C., most preferably 300° C. to 400° C.; the gas space velocity, SV, in the vapor phase reaction is usually within a range of from 100 to 10,000 $hr^{-1}$, preferably 300 to 6,000 $hr^{-1}$, more preferably 300 to 2,000 $hr^{-1}$; the average contact time with the catalyst can be from 0.01 to 10 seconds or more, but is usually in the range of from 0.1 to 10 seconds, preferably from 2 to 6 seconds; the pressure in the reaction zone usually ranges from 0 to 75 psig, but is preferably no more than 50 psig. In a single pass mode process, it is preferred that the oxygen be supplied from an oxygen-containing gas such as air. The single pass mode process may also be practiced with oxygen addition. In the practice of the recycle mode process, oxygen gas by itself is the preferred source so as to avoid the build up of inert gases in the reaction zone.

Of course, in the oxidation reaction of the present invention, it is important that the hydrocarbon and oxygen concentrations in the feed gases be maintained at the appropriate levels to minimize or avoid entering a flammable regime within the reaction zone or especially at the outlet of the reactor zone. Generally, it is preferred that the outlet oxygen levels be low to both minimize after-burning and, particularly, in the recycle mode of operation, to minimize the amount of oxygen in the recycled gaseous effluent stream. In addition, operation of the reaction at a low temperature (below 450° C.) is extremely attractive because after-burning becomes less of a problem which enables the attainment of higher selectivity to the desired products. The catalyst of the present invention operates more efficiently at the lower temperature range set forth above, significantly reducing the formation of acetic acid and carbon oxides, and increasing selectivity to acrylic acid. As a diluting gas to adjust the space velocity and the oxygen partial pressure, an inert gas such as nitrogen, argon or helium may be employed.

When the oxidation reaction of propane, and especially the oxidation reaction of propane and propene, is conducted by the method of the present invention, carbon monoxide, carbon dioxide, acetic acid, etc. may be produced as by-products, in addition to acrylic acid. Further, in the method of the present invention, an unsaturated aldehyde may sometimes be formed depending upon the reaction conditions. For example, when propane is present in the starting material mixture, acrolein may be formed; and when isobutane is present in the starting material mixture, methacrolein may be formed. In such a case, such an unsaturated aldehyde can be converted to the desired unsaturated carboxylic acid by subjecting it again to the vapor phase catalytic oxidation with the promoted mixed metal oxide-containing catalyst of the present invention or by subjecting it to a vapor phase catalytic oxidation reaction with a conventional oxidation reaction catalyst for an unsaturated aldehyde.

In its tenth, eleventh and twelfth aspects, the present invention provides processes for producing an unsaturated nitrile, which comprises subjecting an alkane, or a mixture of an alkane and an alkene, to a vapor phase catalytic oxidation reaction with ammonia in the presence of a catalyst produced in accord with the present invention to produce an unsaturated nitrile.

In regard to the use of a halogen as the promoter element of the catalyst of the present invention, it is possible to add a gaseous halogen source as previously identified to the gas feed to the reaction.

In the production of such an unsaturated nitrile, as the starting material alkane, it is preferred to employ a $C_{3-8}$alkane such as propane, butane, isobutane, pentane, hexane and heptane. However, in view of the industrial application of nitrites to be produced, it is preferred to employ a lower alkane having 3 or 4 carbon atoms, particularly propane and isobutane.

Similarly, as the starting material mixture of alkane and alkene, it is possible to employ a mixture of $C_{3-8}$alkane and $C_{3-8}$alkene such as propane and propene, butane and butene, isobutane and isobutene, pentane and pentene, hexane and hexene, and heptane and heptene. However, in view of the industrial application of nitrites to be produced, it is more preferred to employ a mixture of a lower alkane having 3 or 4 carbon atoms and a lower alkene having 3 or 4 carbon atoms, particularly propane and propene or isobutane and isobutene. Preferably, in the mixture of alkane and alkene, the alkene is present in an amount of at least 0.5% by weight, more preferably at least 1.0% by weight to 95% by weight, most preferably 3% by weight to 90% by weight.

The purity of the starting material alkane is not particularly limited, and an alkane containing a lower alkane such as methane or ethane, air or carbon dioxide, as impurities, may be used without any particular problem. Further, the starting material alkane may be a mixture of various alkanes. Similarly, the purity of the starting material mixture of alkane and alkene is not particularly limited, and a mixture of alkane and alkene containing a lower alkene such as ethene, a lower alkane such as methane or ethane, air or carbon dioxide, as impurities, may be used without any particular problem. Further, the starting material mixture of alkane and alkene may be a mixture of various alkanes and alkenes.

There is no limitation on the source of the alkene. It may be purchased, per se, or in admixture with an alkane and/or other impurities. Alternatively, it can be obtained as a by-product of alkane oxidation. Similarly, there is no limitation on the source of the alkane. It may be purchased, per se, or in admixture with an alkene and/or other impurities. Moreover, the alkane, regardless of source, and the alkene, regardless of source, may be blended as desired.

The detailed mechanism of the ammoxidation reaction of this aspect of the present invention is not clearly understood. However, the oxidation reaction is conducted by the oxygen atoms present in the above promoted mixed metal oxide or by the molecular oxygen in the feed gas. When molecular oxygen is incorporated in the feed gas, the oxygen may be pure oxygen gas. However, since high purity is not required, it is usually economical to use an oxygen-containing gas such as air.

As the feed gas, it is possible to use a gas mixture comprising an alkane, or a mixture of an alkane and an alkene, ammonia and an oxygen-containing gas, However, a gas mixture comprising an alkane or a mixture of an alkane and an alkene and ammonia, and an oxygen-containing gas may be supplied alternately.

When the gas phase catalytic reaction is conducted using an alkane, or a mixture of an alkane and an alkene, and ammonia substantially free from molecular oxygen, as the feed gas, it is advisable to employ a method wherein a part of the catalyst is periodically withdrawn and sent to an oxidation regenerator for regeneration, and the regenerated catalyst is returned to the reaction zone. As a method for regenerating the catalyst, a method may be mentioned wherein an oxidizing gas such as oxygen, air or nitrogen monoxide is permitted to flow through the catalyst in the regenerator usually at a temperature of from 300° C. to 600° C.

These aspects of the present invention will be described in further detail with respect to a case where propane is used as the starting material alkane and air is used as the oxygen source. The proportion of air to be supplied for the reaction is important with respect to the selectivity for the resulting acrylonitrile. Namely, high selectivity for acrylonitrile is obtained when air is supplied within a range of at most 25 moles, particularly 1 to 15 moles, per mole of the propane. The proportion of ammonia to be supplied for the reaction is preferably within a range of from 0.2 to 5 moles, particularly from 0.5 to 3 moles, per mole of propane. This reaction may usually be conducted under atmospheric pressure, but may be conducted under a slightly increased pressure or a slightly reduced pressure. With respect to other alkanes such as isobutane, or to mixtures of alkanes and alkenes such as propane and propene, the composition of the feed gas may be selected in accordance with the conditions for propane.

The processes of these aspects of the present invention may be conducted at a temperature of, for example, from 250° C. to 480° C. More preferably, the temperature is from 300° C. to 400° C. The gas space velocity, SV, in the gas phase reaction is usually within the range of from 100 to 10,000 $hr^{-1}$, preferably from 300 to 6,000 $hr^{-1}$, more preferably from 300 to 2,000 $hr^{-1}$. As a diluent gas, for adjusting the space velocity and the oxygen partial pressure, an inert gas such as nitrogen, argon or helium can be employed. When ammoxidation of propane is conducted by the method of the present invention, in addition to acrylonitrile, carbon monoxide, carbon dioxide, acetonitrile, hydrocyanic acid and acrolein may form as by-products.

EXAMPLES

Preparative

Comparative Example 1

In a 2000 mL rotavap flask containing 300 g of water, 51.4 g of ammonium heptamolybdate tetrahydrate (Aldrich Chemical Company), 10.1 g of ammonium metavanadate (Alfa-Aesar) and 15.4 g of telluric acid (Aldrich Chemical Company) were dissolved upon heating to 70° C. After cooling to 40° C., 267.5 g of an aqueous solution of niobium oxalate (Reference Metals), containing 1.25% Nb was added to the three component mixture to obtain a solution. After removing the water via a rotary evaporator with a warm water bath at 50° C. and 28 mm Hg, the solid materials were further dried in a vacuum oven at 25° C. overnight and then calcined. (Calcination was effected by placing the solid materials in an air atmosphere and then heating them to 275° C. at 10° C./min and holding them under the air atmosphere at 275° C. for one hour; the atmosphere was then changed to argon and the material was heated from 275° C. to 600° C. at 2° C./min and the material was held under the argon atmosphere at 600° C. for two hours.) The catalyst thus obtained was pressed in a mold and then broken and sieved to 10–20 mesh granules for reactor evaluation.

Comparative Example 2

In a 600 mL beaker containing 223 g of water, 24.2 g of oxalic acid were dissolved and then 58.9 g of catalyst powder from Comparative Example 1 were added. This mixture was heated to 75° C. and held at 75° for six hours with stirring. After cooling this mixture to 25° C., the solid materials were collected by vacuum filtration and dried in a vacuum overnight. These dried materials were heated in argon to 600° C. at 2° C./min and held under argon at 600° C. for two hours. The catalyst thus obtained was pressed in a mold and then broken and sieved to 10-20 mesh granules for reactor evaluation.

Example 1

6 g of the catalyst from Comparative Example 2 were impregnated with 1.72 g of samarium in 5% $HNO_3$ and 5.2 g water followed by drying via rotavap at 50° C. and further drying in a vacuum oven at 25° C. overnight. These dried materials were then calcined by placing the solid materials in an air atmosphere and then heating them to 275° C. at 10° C./min and holding them under the air atmosphere at 275° C. for one hour; the atmosphere was then changed to argon and the material was heated from 275° C. to 600° C. at 2° C./min and the material was held under the argon atmosphere at 600° C. for five hours. The final catalyst had a nominal composition of $Mo_{1.0}V_{0.3}Te_{0.23}Nb_{0.125}Sm_{0.0025}O_x$. The catalyst thus obtained was pressed in a mold and then broken and sieved to 10–20 mesh granules for reactor evaluation.

Example 2

6 g of the catalyst from Comparative Example 2 were impregnated with 3.37 g of samarium in 5% $HNO_3$ and 3.5 g water followed by drying via rotavap at 50° C. and further drying in a vacuum oven at 25° C. overnight. These dried materials were then calcined by placing the solid materials in an air atmosphere and then heating them to 275° C. at 10° C./min and holding them under the air atmosphere at 275° C. for one hour; the atmosphere was then changed to argon and the material was heated from 275° C. to 600° C. at 2° C./min and the material was held under the argon atmosphere at 600° C. for five hours. The final catalyst had a nominal composition $Mo_{1.0}V_{0.3}Te_{0.23}Nb_{0.125}Sm_{0.005}O_x$. The catalyst thus obtained was pressed in a mold and then broken and sieved to 10–20 mesh granules for reactor evaluation.

Example 3

6 g of the catalyst from Comparative Example 2 were impregnated with 6.85 g of samarium in 5% $HNO_3$ followed by drying via rotavap at 50° C. and further drying in a vacuum oven at 25° C. overnight. These dried materials were then calcined by placing the solid materials in an air atmosphere and then heating them to 275° C. at 10° C./min and holding them under the air atmosphere at 275° C. for one hour; the atmosphere was then changed to argon and the material was heated from 275° C. to 600° C. at 2° C./min and the material was held under the argon atmosphere at 600° C. for five hours. The final catalyst had a nominal composition of $Mo_{1.0}V_{0.3}Te_{0.23}Nb_{0.125}Sm_{0.01}O_x$. The catalyst thus obtained was pressed in a mold and then broken and sieved to 10–20 mesh granules for reactor evaluation.

Evaluation and Results

Catalysts were evaluated in a 10 cm long Pyrex tube reactor (internal diameter: 3.9 mm). The catalyst bed (4 cm long) was positioned with glass wool at approximately mid-length in the reactor and was heated with an electric furnace. Mass flow controllers and meters regulated the gas flow rate. The oxidation was conducted using a feed gas stream of propane, steam and air, with a feed ratio of propane:steam:air of 1:3:96. The reactor effluent was analyzed by an FTIR. The results (along with the reaction temperature and residence time) are shown in Table 1. In all cases, the propane conversion (%), acrylic acid yield (%) and selectivity to acrylic acid (%) were higher for the catalysts consisting of the promoter added to the annealed surface (Examples 3–5) when compared to the unpromoted catalyst (Example 2) and the catalyst without acid treatment (Example 1).

TABLE 1

| | Reaction Temperature (° C.) | Residence Time (sec.) | Propane Conversion (%) | Acrylic Acid Yield (%) | Selectivity to Acrylic Acid (%) |
|---|---|---|---|---|---|
| Comp. Ex. 1 | 390 | 3 | 71 | 13 | 18 |
| Comp. Ex. 2 | 390 | 3 | 38 | 29 | 77 |
| Ex. 1 | 390 | 3 | 39 | 38 | 98 |
| Ex. 2 | 390 | 3 | 45 | 41 | 91 |
| Ex. 3 | 390 | 3 | 50 | 42 | 84 |

What is claimed is:

1. A process for preparing an improved catalyst, said process comprising:
   (a) providing a mixed metal oxide having the empirical formula

   $A_aV_bN_cX_dO_e$ wherein A is at least one element selected from the group consisting of Mo and W, N is at least one element selected from the group consisting of Te, Sb and Se, and X is at least one element selected from the group consisting of Nb, Ta, Ti, Al, Zr, Cr, Mn, Fe, Ru, Co, Rh, Ni, Pt, Bi, B, In, Ce, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu,
   wherein A, V, N and X are present in such amounts that the atomic ratio of A:V:N:X is a:b:c:d, and
   wherein, when a=1, b=0.01 to 2, c=0.01 to 1, d=0.01 to and e is dependent on the oxidation state of the other elements;
   (b) contacting said mixed metal oxide with a liquid contact member selected from the group consisting of organic acids, alcohols, inorganic acids and hydrogen peroxide to form a contact mixture;
   (c) recovering insoluble material from said contact mixture;
   (d) calcining said recovered insoluble material in a non-oxidizing atmosphere;
   (e) admixing said calcined recovered insoluble material with
      (i) at least one promoter element or compound thereof, wherein said at least one promoter element is selected from the group consisting of Au, Ag, Re, Pr, Zn, Ga, Pd, Ir, Nd, Y, Sm, Tb, Br, Cu, Sc, Cl, F and I, and
      (ii) at least one solvent for said promoter element or compound thereof to form an admixture;
   (f) removing said at least one solvent from said so-formed admixture to form a catalyst precursor; and
   (g) calcining said catalyst precursor.
2. A catalyst produced by the process according to claim 1.

* * * * *